(12) United States Patent
Drzewiecki et al.

(10) Patent No.: US 6,338,719 B1
(45) Date of Patent: Jan. 15, 2002

(54) METHOD AND SYSTEM FOR DETECTING VASCULAR CONDITIONS USING AN OCCLUSIVE ARM CUFF PLETHYSMOGRAPH

(75) Inventors: Gary M. Drzewiecki, Princeton, NJ (US); Robert B. Drzewiecki, East Amherst, NY (US)

(73) Assignee: Rutgers, The State University of New Jersey, Piscataway, NJ (US)

( * ) Notice: Subject to any disclaimer, the term of this patent is extended or adjusted under 35 U.S.C. 154(b) by 0 days.

(21) Appl. No.: 09/591,872

(22) Filed: Jun. 12, 2000

(51) Int. Cl.$^7$ ................................................. A61B 5/02
(52) U.S. Cl. ....................................... 600/490; 600/485
(58) Field of Search ............................... 600/490, 485, 600/495

(56) References Cited

U.S. PATENT DOCUMENTS

| | | | |
|---|---|---|---|
| 5,054,494 A | * 10/1991 | Lazzaro et al. | 128/677 |
| 5,343,867 A | * 9/1994 | Shankar | 128/668 |
| 5,680,867 A | * 10/1997 | Shimazu et al. | 128/672 |
| 5,997,476 A | * 12/1999 | Brown | 600/300 |
| 6,152,881 A | * 11/2000 | Raines et al. | 600/507 |

OTHER PUBLICATIONS

*Noninvasive Measurement of the Human Brachial Artery Pressure—Area Relation In Collapse and Hypertension,* by Gary Drzewiecki and James J. Pilla, Rutgers University, Biomedical Engineering Department, revised manuscript #97144—Apr. 30, 1998.

*Noninvasive Measurement of Brachial Artery Compliance Variability,* by Robert Andor Linden and Gary Drzewiecki, Rutgers University, Biomedical Engineering Department.

* cited by examiner

*Primary Examiner*—Robert L. Nasser
*Assistant Examiner*—Patricia Mallari
(74) *Attorney, Agent, or Firm*—Dilworth & Barrese, LLP

(57) ABSTRACT

A method and system are provided for detecting various vascular conditions using an occlusive arm cuff plethysmograph. The system includes data acquisition hardware, including the occlusive arm cuff plethysmograph, for obtaining arterial and endothelial function data from a patient, processing means utilizing application or analysis software for analyzing the arterial and endothelial function data, and a database of computer models, such as brachial artery pressure versus lumen area curves (P-A curves) and brachial artery pressure versus compliance curves (P-C curves), developed by analyzing data for a plurality of subjects where their vascular conditions were known. The processing means diagnoses and predicts various vascular conditions pertaining to the patient by comparing or correlating the analyzed arterial and endothelial function data with the computer models stored within the database and presents the findings on a display.

25 Claims, 9 Drawing Sheets

Pressure–volume curves for normotensive (h) and hypertensive subjects (b)

METHOD AND SYSTEM FOR DETECTING VASCULAR CONDITIONS USING AN OCCLUSIVE ARM CUFF PLETHYSMOGRAPH

BACKGROUND OF THE INVENTION

1. Field of the Invention

The present invention relates to a noninvasive method and system for detecting various vascular conditions. More particularly, the present invention relates to a noninvasive method and system which utilizes an occlusive arm cuff as a plethysmograph to obtain arterial and endothelial data on a patient and to analyze the data for diagnosing and predicting various vascular conditions.

2. Description of the Related Art

An occlusive arm cuff capable of being filled with compressible air is routinely used to determine the arterial blood pressure. It has been proposed to also use the occlusive arm cuff as a plethysmograph, i.e., to measure the arterial volume, since it possesses compliance due to the fact that it is filled with compressible air. In theory, if the cuff compliance is known, the arterial pulsations, that are found in the cuff pressure, can be converted into the arterial volume pulse which can be used to measure arterial volume to render the occlusive arm cuff as a plethysmograph.

Unfortunately, cuff compliance is not a constant value. It is dependent on how tightly the arm cuff is wrapped on the subject's arm and the current level of cuff pressure. This has prevented the use of the occlusive arm cuff as a plethysmograph.

The benefit of simultaneously measuring the arterial volume and pressure by means of the occlusive arm cuff is the ability to find arterial mechanics and wall properties. Such arterial information could then be obtained on patients as part of a routine physical exam. Furthermore, arterial wall properties can provide an early indication of the presence of a vascular disease process.

U.S. patent application Ser. No. 09/205,042 filed on Dec. 3, 1998 by Drzewiecki et al. and having a common assignee with the present application describes a method of calibrating the occlusive arm cuff to measure arterial volume to allow the arm cuff to be used as a plethysmograph. With reference to FIG. 1, there is shown a block diagram of the prior art occlusive arm cuff plethysmograph designated generally by reference numeral 100. The occlusive arm cuff plethysmograph includes a pump 102, a needle valve 104, a flow meter 106, a blood pressure cuff 108, and a pressure transducer 110. Pump 102 provides a constant known volume of gas per pump stroke over the relevant pressure range. The output signal from the transducer 110 is connected to an electronic amplifier 111, which in turn is connected to an analog-to-digital (A/D) converter and signal processing circuit 112. The A/D converter 112 outputs a first component 118 and a second component 120. The first component 118 is caused by compressed air in the arm cuff 108 by the pump 102. The second component 120 is caused by the patient's arterial pulse. A motor speed control circuit 113 controls the frequency of the pump 102. A power supply 114 provides power to motor speed control circuit 113.

One typically begins the process by ascertaining the stroke volume of pump 102. This can be done by measuring the volume of a fluid (e.g., a gas, such as air) pumped by pump 102 over a period of time (e.g., ten seconds) divided by the number of strokes during that period of time. The fluid used to ascertain the stroke volume of pump 102 is typically the same fluid as that used to inflate the arm cuff 108 during use of the arm cuff 108. This process can take place simultaneously with data acquisition and is monitored throughout the data acquisition procedure by using the flow meter 106 and monitoring the signal received at the pressure transducer 110.

In short, the method entails applying a known volume change to the arm cuff using a periodic pump and subsequently requiring a skilled operator to calculate the cuff compliance. Since the pump frequency and the arterial pulse frequency differ, electronic filtering is used to separate each pulse from the cuff pressure. This method, thus provides continuous measurement of cuff compliance, thereby solving the cuff compliance problem. The method is referred to as occlusive arm cuff plethysmography.

In short, the occlusive arm cuff, acting as a plethysmograph, measures the arterial volume pulse as cuff pressure is decreased. In this manner the brachial artery compliance can be measured over the full range of cuff pressures. This allows the examination of all three states of the artery: collapse, buckling and distension.

To find the arterial compliance, one divides the arterial volume pulse by the arterial pulse pressure according to, $$C(P_t) = \frac{\Delta V}{(P_{systolic} - P_{diastolic})W_{cuff}}$$

$P_{systolic}$ and $P_{diastolic}$ are the systolic and diastolic pressure obtained from the Korotkoff method. $P_t$ is the arterial transmural pressure found from the difference between mean arterial pressure and mean cuff pressure, $$P_t = \overline{P_a} - \overline{P_{cuff}}$$

$W_{cuff}$ is a constant that represents the cuff width. More precisely, it represents the actual volume of artery that is subjected to a uniform transmural pressure, $P_t$.

The lumen area can be found by integrating the compliance curve, from negative infinity to $P_t$, $$A(P_t) = \int C(P_t) dP_t$$

where negative infinity is approximated by the lowest transmural pressure measured or when the arterial lumen is completely collapsed. Since complete collapse corresponds with a lumen area equal to zero, the initial constant of this integration is zero as well. This analysis permits the determination of lumen area from noninvasive compliance measurements.

Other parameters can also be determined, such as the volume of a segment of an artery by integrating the arterial compliance, and blood flow through the artery by multiplying the derivative of the arterial volume with respect to time with the arterial compliance.

In one study, the occlusive arm cuff plethysmography was employed to derive brachial artery pressure (arterial pressure) versus lumen area curves (P-A curves) for several subjects. Drzewiecki et al., "Noninvasive Measurement of the Human Brachial Artery Pressure—Area Relation In Collapse and Hypertension," Annals of Biomed. Eng., vol. 26, pages 965–974, 1998. A P-A curve for a normotensive and hypertensive subject are shown by FIG. 2. It is apparent from this data that the P-A curves are quite varied from subject to subject. First, the vessel is most compliant near zero pressure (i.e., when the blood pressure in the artery equals cuff pressure). Second, the brachial artery adapts to high blood pressure by increasing its lumen size. Hence, a single observation of the P-A curve in a given subject may be insufficient for diagnostic information. Accordingly, multiple observations of the same patient or perhaps the use of an intervention may be required.

The cross-section of normal, hypertensive and arteriosclerotic blood vessel changes are shown by FIG. 3. It is apparent that the vascular smooth muscle wall 2 of the hypertensive vessel becomes thicker and the lumen 4 becomes larger or remains the same. The lumen 4 of an arteriosclerotic vessel simply becomes narrower due to plaque 6 lining the wall 2. An important application of the occlusive arm cuff plethysmograph is to aid in the noninvasive detection of these important vessel changes, i.e., to measure smooth muscle or endothelial function. It is not certain how these conditions manifest themselves in the P-A curve or in a brachial artery pressure versus compliance curve (P-C curve) which represent a patient's resting arterial mechanical function.

Due to the presence of arterial wall smooth muscle, the subject's P-A and P-C curves may vary with muscle activity. Thus, the vascular smooth muscle is a part of the vascular function that must be examined. Prior research suggests that impaired muscle function, often termed as endothelial function, is predictive of atherosclerosis.

Hence, there is a need for additional research directed at measuring subjects known to possess various types of vascular conditions and to develop computer models that can predict or analyze changes in the P-A, P-C curves and other data. This will aid in diagnosis of the patient, since the specific alterations associated with a particular vascular condition can be recognized from the curve patterns. For example, research indicates that the arterial function is impaired in the presence of vascular disease, such as arteriosclerosis.

A need also exists in developing a cost effective process which employs a new instrument (based on this technology) that utilizes the conventional occlusive arm cuff to noninvasively measure the functional, geometrical, and mechanical condition of a patient's arterial and endothelial function and to diagnose and predict various vascular conditions based on the computer models. Such a medical instrument can become part of routine patient physical examination. Currently, only more costly imaging techniques are available.

Additionally, a need also exists to incorporate the medical instrument into an existing automatic blood pressure monitor that employs an occlusive arm cuff to allow the blood pressure monitor to gather arterial and endothelial function information, where the medical instrument uses programmable instructions to determine cuff compliance of the arm cuff from physical laws of air flow and cuff pressure data. Hence, an operator of the instrument does not need to be mathematically skilled in calculating the cuff compliance.

SUMMARY OF THE INVENTION

The present invention provides a method and system for detecting various vascular conditions using an occlusive arm cuff plethysmograph. The system includes data acquisition hardware, including the occlusive arm cuff plethysmograph, for obtaining arterial and endothelial function data from a patient, processing means utilizing application or analysis software for analyzing the arterial and endothelial function data, and a database of computer models, such as brachial artery pressure versus lumen area curves (P-A curves) and brachial artery pressure versus compliance curves (P-C curves), developed by analyzing data for a plurality of subjects where their vascular conditions were known. The application software further diagnoses and predicts various vascular conditions pertaining to the patient by comparing or correlating the analyzed arterial and endothelial function data with the computer models stored within the database and presents the findings on a display.

In particular, the system of the present invention for determining at least one vascular condition includes the occlusive arm cuff plethysmograph having means for obtaining patient vascular data and means for outputting the patient vascular data; at least one database storing predetermined vascular data and a plurality of corresponding vascular conditions; and at least one processor.

The system further includes a plurality of programmable instructions, executed by the at least one processor, for determining compliance of the arm cuff from physical laws of air flow and cuff pressure data and for correlating the patient vascular data with the predetermined vascular data stored within the at least one database. The at least one processor then determines at least a portion of the predetermined vascular data which exhibits the maximum correlation with the patient vascular data. The at least one vascular condition is determined to be at least one of the plurality of corresponding vascular conditions which corresponds to a portion of the predetermined vascular data. The occlusive arm cuff plethysmograph further has means for connecting to a conventional blood pressure monitor, such that it uses the arm cuff provided by the blood pressure monitor.

BRIEF DESCRIPTION OF THE DRAWINGS

Preferred embodiments of the invention are described below with reference to the drawings, which are described as follows.

DETAILED DESCRIPTION OF THE PREFERRED EMBODIMENTS

The method and system of the present invention processes vascular data obtained via an occlusive arm cuff of an occlusive arm cuff plethysmograph to diagnose and predict various vascular conditions, such as hypertension and arteriosclerosis. An occlusive arm cuff plethysmograph is described in U.S. patent application Ser. No. 09/205,042 filed on Dec. 3, 1998 by Drzewiecki et al. having a common assignee with the present application; the contents of which are incorporated herein by reference.

This application also describes various equations for computing various parameters, such as arterial volume compliance, arterial area compliance, and arterial lumen area. In the present invention, these equations have been translated into a series of programmable instructions which are stored within a data storage medium and processed by at least one processor for determining various vascular conditions of a patient.

Figure 4:
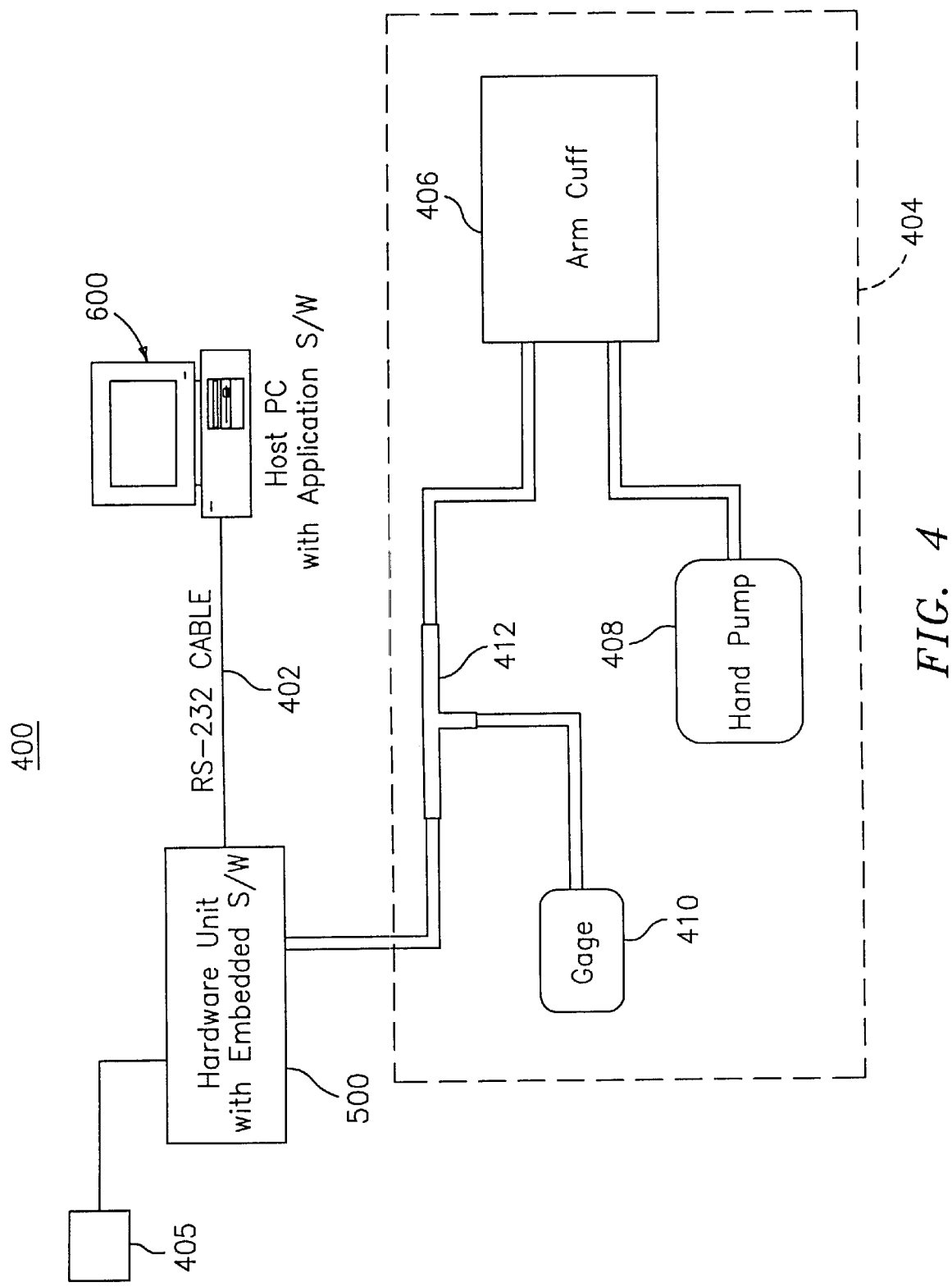
FIG. 4 is a block diagram of the system architecture of the present invention showing a hardware unit with embedded software and a personal computer (PC) with application software.

With reference to FIG. 4, there is shown a block diagram of the system architecture of the present invention, designated generally by reference numeral 400. The system 400 includes a hardware unit with embedded software 500 and a blood pressure monitor 404 connected to the hardware unit 500. The hardware unit 500 and the blood pressure monitor 404 collectively form an occlusive arm cuff plethysmograph. The blood pressure monitor 404 is preferably a conventional blood pressure monitor used to measure a patient's blood pressure having an arm cuff 406 connected to a hand pump 408 and a pressure gage 410 via a T-connector 412. The T-connector 412 is used to place a pressure transducer 502 (see FIG. 5) of the hardware unit 500 in line with the existing pressure gage 410. Accordingly, the system of the present invention considers the ease of application by a user, since the familiar arm cuff, hand pump and pressure gage of a conventional blood pressure monitor are used.

The system 400 is powered by a power supply 405 connected to the hardware unit 500. The hardware unit 500 is connected to the output tube from the arm cuff 406 that is typically connected to the pressure gage 410 in the conventional blood pressure monitor. The hardware unit 500 is further preferably connected via an RS-232 cable 402 (i.e., a serial connection) to a personal computer (PC) 600 having application or analysis software stored therein.

Figure 5:
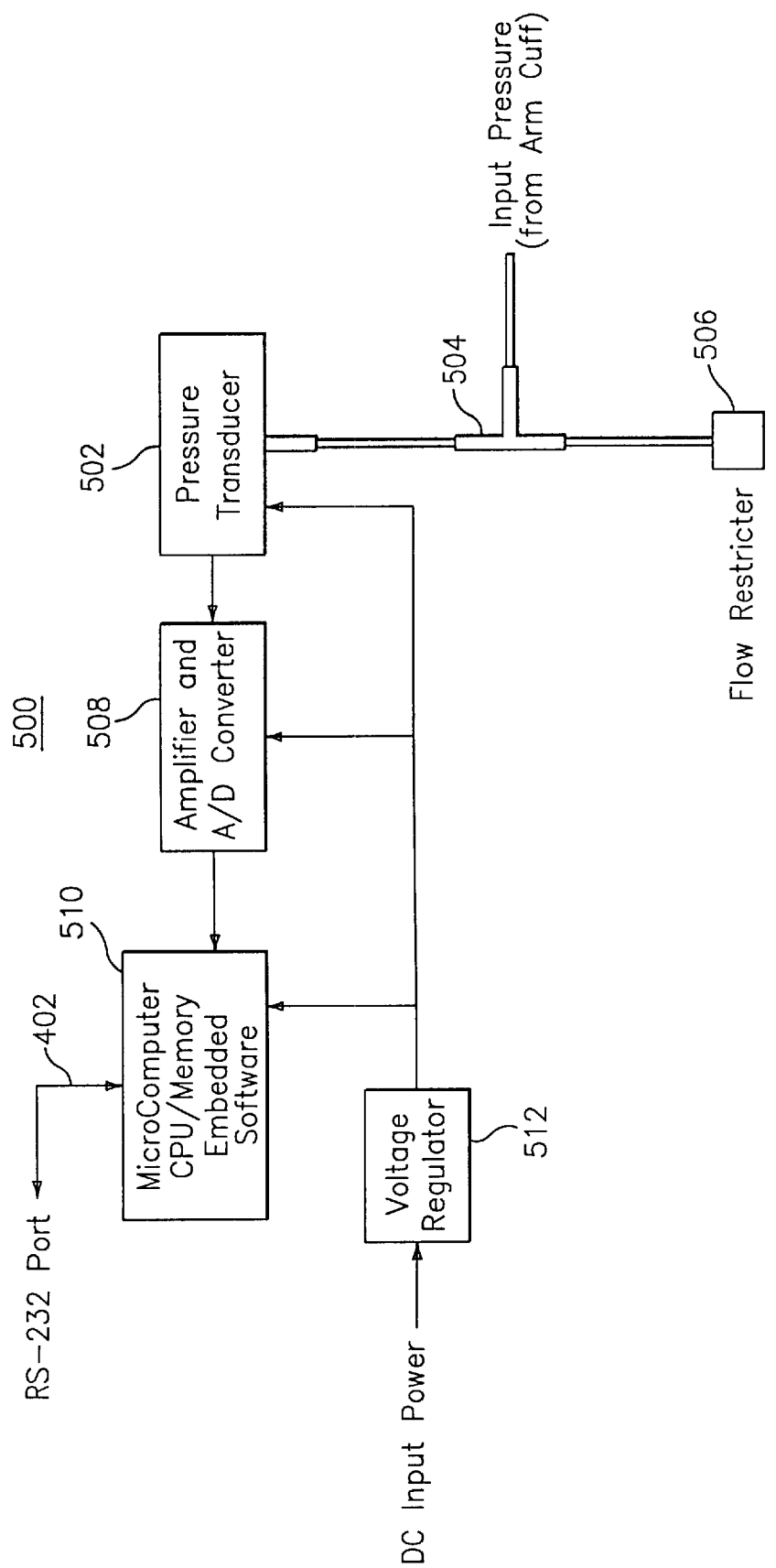
FIG. 5 is a block diagram of the components of the hardware unit shown by FIG. 4.

With reference to FIG. 5, there are shown the components of the hardware unit 500. The hardware unit 500 includes the pressure transducer 502 which is connected via a T-connector 504 to an output of a flow restrictor 506 and an output of the arm cuff 406, i.e., the input pressure from T-connector 412 (see FIG. 4). The outputs of the pressure transducer 502 are inputted to an amplifier and A/D converter 508. The outputs of the A/D converter 508 are inputted to a microcomputer or processor with embedded application or analysis software 510 stored therein. Input power is fed to a voltage regulator 512 which in turn provides at least one voltage regulation signal to the pressure transducer 502, the A/D converter 508 and the microcomputer 510.

Figure 6:
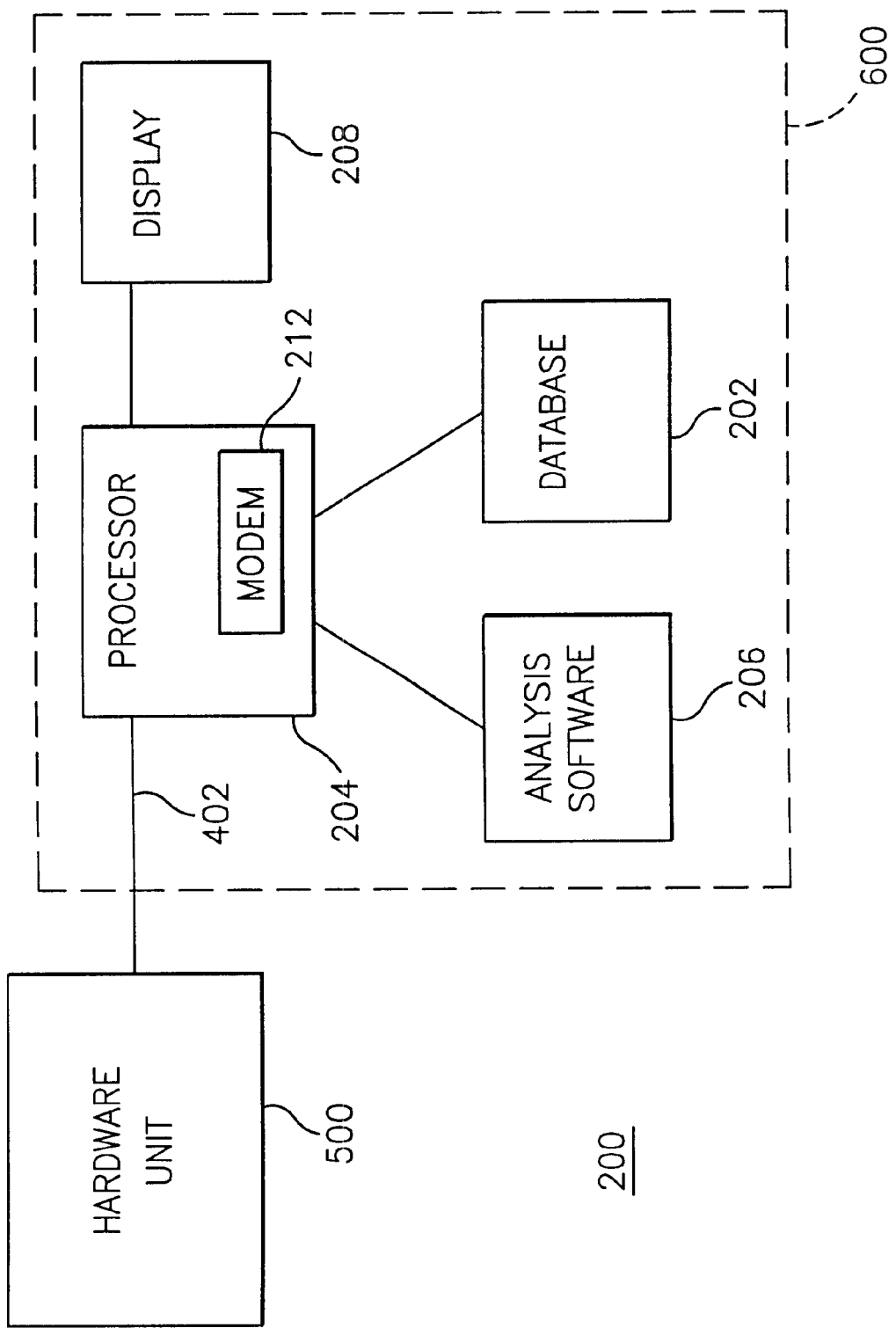
FIG. 6 is a block diagram of the components of the personal computer (PC) shown by FIG. 4.
Figure 7:
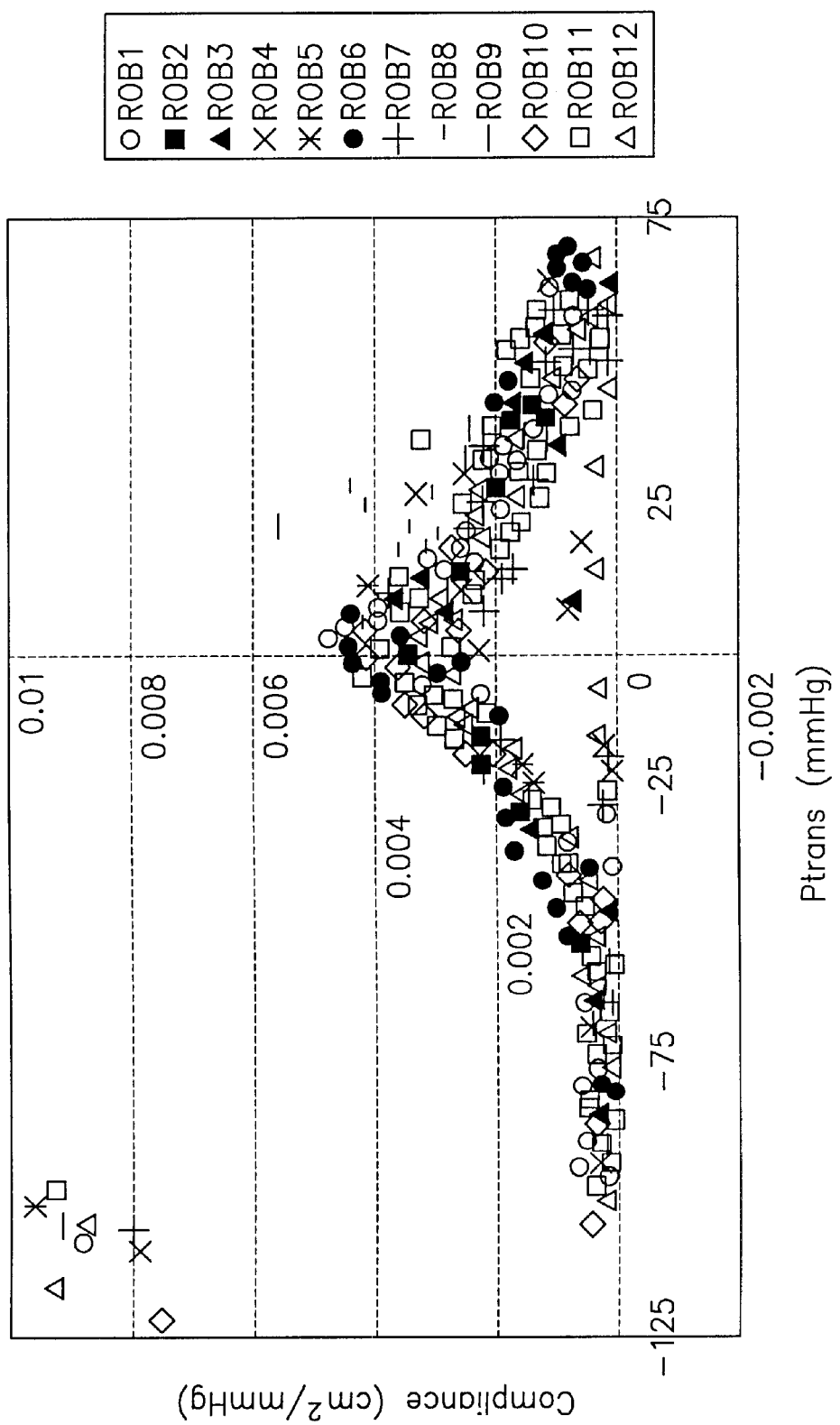
FIG. 7 illustrates pressure-compliance curves for a single subject created by the system of the present invention during a period of 22 days.

With reference to FIG. 6, there are shown the components of the PC 600. The PC 600 includes a database of computer models 202, such as brachial artery pressure versus lumen area curves (P-A curves) and brachial artery pressure versus compliance curves (P-C curves), for a plurality of subjects where their vascular conditions were known. Examples of P-C curves created by the present invention over a period of 22 days and corresponding to a single patient are shown by FIG. 7.

The computer models are preferably created by taking arterial measurements using the system of the present invention from subjects who are known to have certain vascular conditions. The arterial measurements are then used to create the P-A and P-C curves using equations known in the art which have been translated into a series of programmable instructions and stored within a memory. The curves are then categorized according to a particular vascular condition and are stored in the database of computer models 202.

Figure 3:
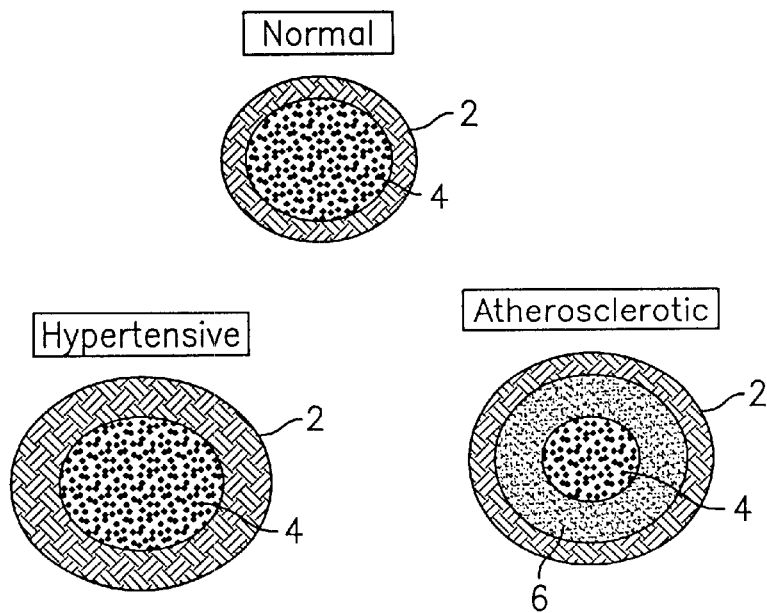
FIG. 3 illustrates cross-sections of the observed changes in an artery during both hypertension and atherosclerosis.

It is contemplated that other data is stored within the database of computer models 202, such as tables of arterial function data and observations made of the P-A and P-C curves. For example, the P-C curve shows that the brachial artery compliance increases and shifts towards high pressure as hypertension increases. Further, the P-A curve shows that the lumen area of a hypertensive patient increases as the transmural pressure increases as compared to a normotensive subject (see FIG. 3). These tables and observations can be stored within the database of computer models 202 to further aid in analyzing the vascular data obtained from the patient.

As an example, in order to create a P-A curve, the arterial area compliance or compliance per unit length is determined by dividing the arterial volume pulse by the pulse pressure for every step decrement in cuff pressure according to, $$C(P_t) = \frac{\Delta V}{(P_{systolic} - P_{diastolic})W_{cuff}}$$

$P_{systolic}$ and $P_{diastolic}$ are the systolic and diastolic pressure obtained from the Korotkoff method. $P_t$ is the arterial transmural pressure found from the difference between mean arterial pressure and mean cuff pressure, $$P_t = \overline{P_a} - \overline{P_{cuff}}$$

$W_{cuff}$ is a constant that represents the cuff width. More precisely, it represents the actual volume of artery that is subjected to a uniform transmural pressure, $P_t$. The P-A curve is obtained by integrating the compliance data. The P-C curve is obtained by plotting the compliance data versus the cuff pressure data.

With continued reference to FIG. 6, at least one processor 204 of the personal computer (PC) 600 is capable of utilizing application or analysis software 206 stored therein to analyze arterial and endothelial function data obtained about a subject via the system 400 of the present invention. The analysis software 206 includes a series of programmable instructions for calculating various vascular parameters based on the readings obtained by the system 400.

The at least one processor 204 diagnoses and predicts various vascular conditions pertaining to the patient by correlating the analyzed arterial function data with the computer models stored within the database 202 and preferably, presents the findings on a display 208. Accordingly, as set forth below, the system 400 of the present invention can, for example, noninvasively show that there is a strong potential of a patient developing coronary or cerebral vascular disease once a stenotic lesion has been located in the peripheral vasculature. Hence, the system 400 of the present invention provides noninvasive assessment of cardiovascular risk.

It is contemplated to provide the database 202 in a remote location and provide the at least one processor 204 with a network data connection feature, e.g., by connecting a modem 212 to the at least one processor 204 or some other network data connection device, for accessing the database 202 after analyzing the arterial and endothelial data. It is contemplated that the network data connection may be an internet connection, a wide-area network (WAN) or a local-area network (LAN) connection, a switched network connection, e.g., by utilizing the Public Switched Telephone Network (PSTN), a wireless connection, such as a cellular connection, or some other type of network connection.

It is further contemplated that the arterial and endothelial data obtained by the system 400 is transmitted to a central station which includes processing means and the database of computer models 202 for analyzing the arterial and endothelial data according to the computer models. The analyzed data and results are then transmitted from the central station to the system 400 of the present invention where it is outputted and/or stored. It is also contemplated that hardware unit 500 is implemented within the PC 600 and the PC 600 includes a serial I/O port to couple the PC 600 to the T-connector 412.

In operation, the occlusive arm cuff 406 is placed around a patient's arm. Then, the arm cuff 406 is pressurized normally via the hand pump 408, while the pressure is bled off slowly internal to the hardware unit 500 using the flow restrictor 506. While this is happening, pressure transducer 502 measures the pressure in the arm cuff 406 and the A/D converter 508 senses the pressure increase and begins storing pressure data provided by the pressure transducer 502 in memory resident in the microcomputer 510. The flow algorithms of the embedded software within the microcomputer 510 measure the volume of air (e.g., in liters per minute) out of the air release flow restrictor 506 and additional algorithms, as outlined below, continuously determine the occlusive arm cuff compliance to operate the occlusive arm cuff 406 as an occlusive arm cuff plethysmograph.

Accordingly, the fundamental operation of the occlusive arm cuff plethysmograph rests on the continual determination of its cuff compliance, $C_{cuff}$. This permits the noninvasive measurement of the arterial volume change $\Delta V$ to find arterial compliance. The following relationship is used to find the arterial volume change from cuff pressure change, $\Delta P_{cuff}$, $$\Delta V = \Delta P_{cuff} C_{cuff}$$

In the present invention, the value of $C_{cuff}$ is determined by the concept that the airflow out of the arm cuff 406 during deflation is proportionate to the rate of change of cuff pressure with respect to time. Mathematically, this is written as:

$$\frac{dP_{cuff}}{dt} = \frac{Q}{C_{cuff}}$$

where Q is the airflow out of the arm cuff 406. The value of this approach can be seen that the constant of proportionality is the inverse of cuff compliance. Since the airflow out of the arm cuff 406 is controlled by the airflow restrictor, physics can be employed to find the airflow from the cuff pressure. A typical flow restrictor can be modeled by the following relationship, $$P_{cuff} = (R_1 Q + R_2) Q$$

where $R_1$ and $R_2$ are constants related to the type and size of flow orifice. For a laminar flow restrictor, $R_1$ is small and the relationship is then substituted into the cuff compliance equation to yield, $$\frac{dP_{cuff}}{dt} = \frac{P_{cuff}}{R_2 C_{cuff}}$$

In the case of a needle valve or flow orifice, the flow-squared term is large so that $R_2$ is small and the following cuff compliance relation applies, $$\frac{dP_{cuff}}{dt} = \frac{\sqrt{P_{cuff}}}{C_{cuff}\sqrt{R_1}}$$

For these two cases, the equations can be rearranged to solve for cuff compliance as follows, $$C_{cuff} = P_{cuff}/[R_2 * dP_{cuff}/dt] \text{ or } C_{cuff} = \sqrt{P_{cuff}}/[dP_{cuff}/dt * \sqrt{R_1}]$$

Finally, these equations are replaced with their discrete algorithm forms for implementation in computer software, as shown here, $$C_{cuff} = [P_{cuff}[i-1] * \Delta t]/(R_2[P_{cuff}[i] - P_{cuff}[i-1]]) \quad \text{(Equation A)}$$

or $$C_{cuff} = \sqrt{P_{cuff}[i-1]} * \Delta t / \sqrt{R_1}[P_{cuff}[i] - P_{cuff}[i-1]]) \quad \text{(Equation B)}$$

where i indicates the iteration index and $\Delta t$ is the data sample period.

Equation A or B are then used to continuously determine the cuff compliance from measurements of cuff pressure and valve flow resistance parameter, R. A few methods of applications include altering the structure of the flow restrictor 506. For example, in one application the flow restrictor 506 includes a needle valve as supplied with a conventional blood pressure cuff kit. In this case, Equation B is employed. However, since the valve resistance is unknown, because it is user adjustable, only relative cuff compliance and therefore, relative changes in arterial compliance and lumen area can be measured.

In another application, the flow restrictor 506 includes a fixed needle valve. In this case, Equation B is also used. The needle valve is adjusted to the standard deflation rate of 2 to 3 mm Hg/second. It is then fixed in place. The valve flow resistance is obtained from direct measurements of the valve pressure and flow. The measured value of R is inserted into the computer program. Therefore, each program is calibrated to their corresponding valve.

Further, in another application, a fixed size of flow orifice provides the user with an automatically calibrated cuff plethysmograph. A fixed flow orifice possesses a predetermined value of resistance. This value can be inserted into the computer software. As long as the user employs the specified orifice, the software and cuff apparatus will be calibrated. A fixed orifice requires Equation B for proper calibration of cuff compliance. In a preferred design, the orifice size has a 0.008 inch circular diameter. The corresponding resistance value for this size is 4.79.

Figure 8:
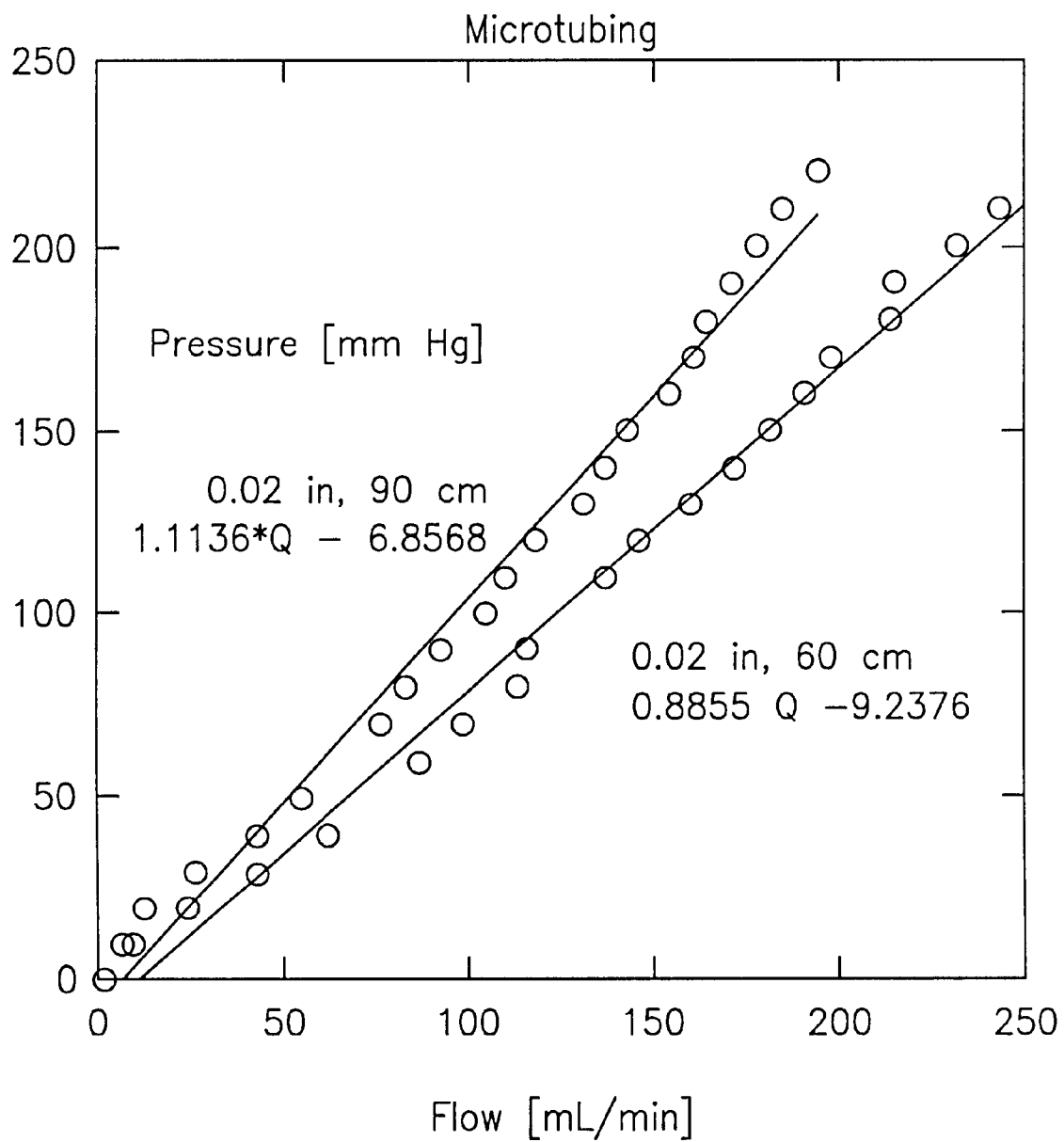
FIG. 8 illustrates pressure-flow data obtained from a flow restrictor fitted with micro-bore tubing and provided within the system of the present invention.

Finally, in other application, a laminar flow device is employed having a laminar flow resistance. In this application, Equation A is employed for continuously determining cuff compliance. In this particular application, the arm cuff 406 is deflated through a length of plastic micro-bore tubing provided within the flow restrictor 506. This results in near laminar flow, provided that the length is sufficient to establish laminar flow. FIG. 8 illustrates pressure-flow data obtained from a flow restrictor fitted with micro-bore tubing. Two different tubing dimensions are shown. Laminar flow is indicated since the pressure and flow relationship fits well to a straight line. In practice, it has been determined that a 0.02 inch diameter micro-tubing of length 90 cm is appropriate. A resistance value of 1.11 is used in Equation A. Provided that the user employs this specific dimension of micro-bore tubing and this resistance value, the cuff plethysmograph and software will be calibrated accurately.

Figure 1:
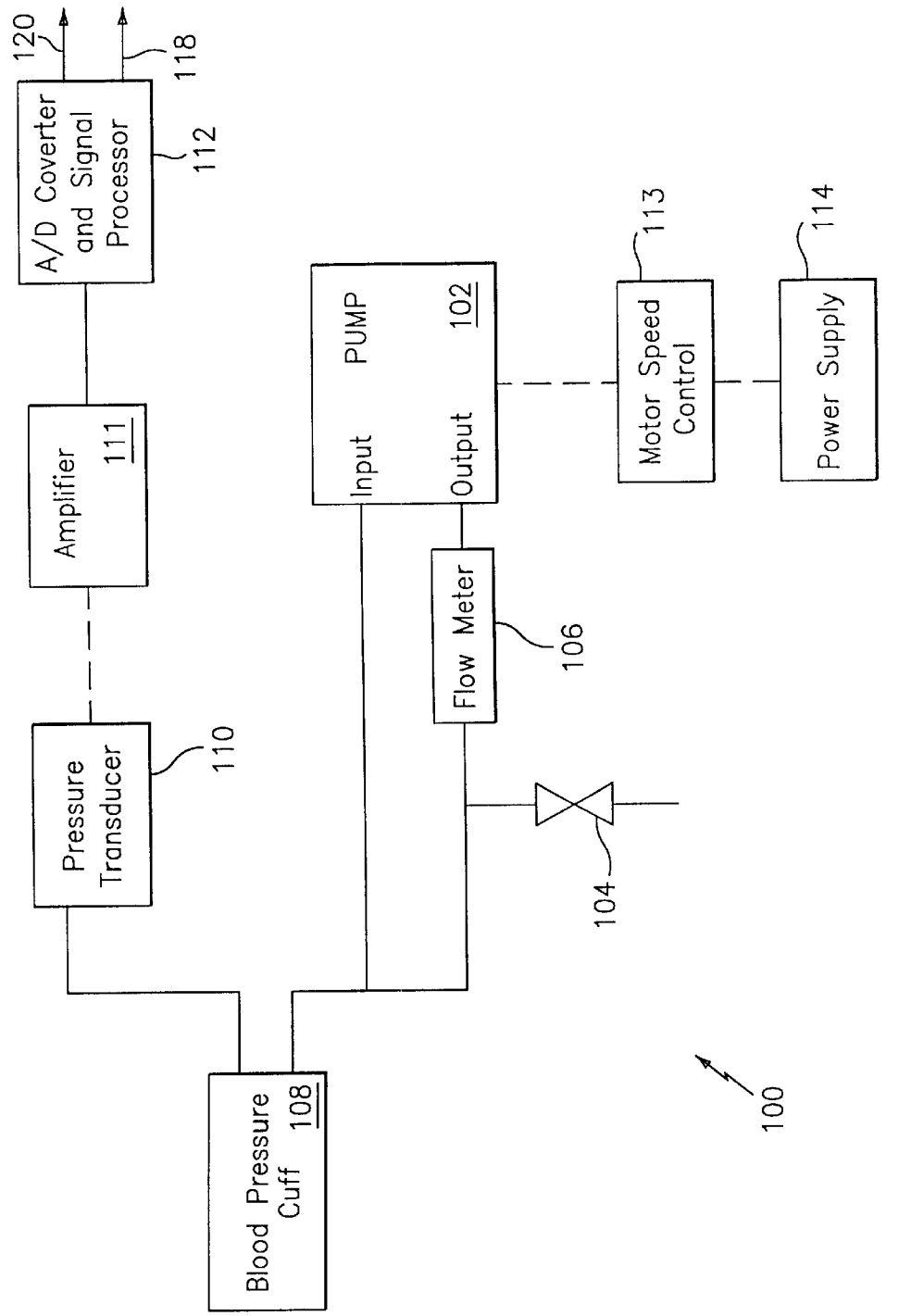
FIG. 1 is a block diagram of a prior art occlusive arm cuff plethysmograph.
Figure 2:
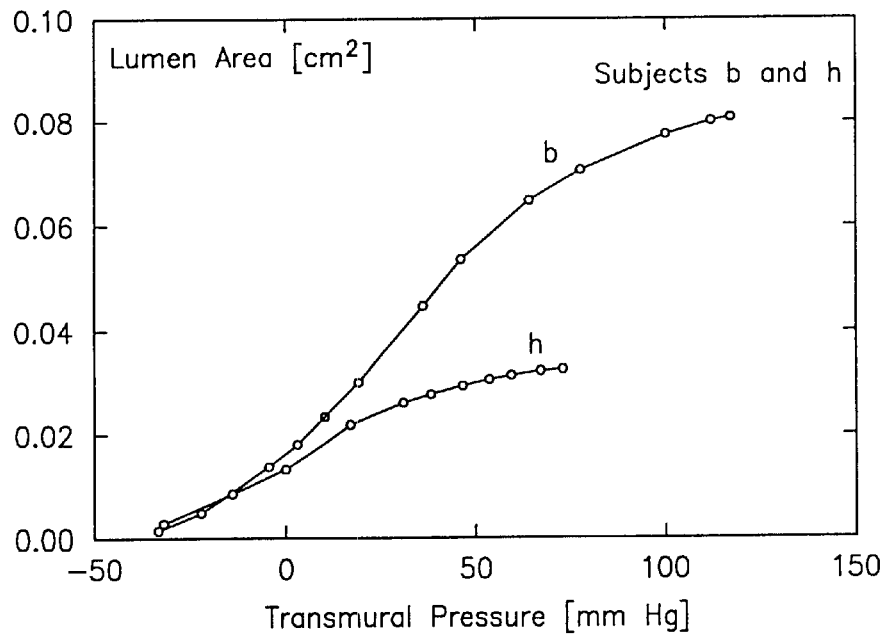
FIG. 2 illustrates pressure-volume curves for normotensive (h) and hypertensive subjects (b)

Accordingly, it has been shown that the present invention is able to calibrate cuff compliance without requiring a pump as in the prior art occlusive arm cuff plethysmograph shown by FIG. 1. The system of the present invention essentially requires a standard blood pressure cuff apparatus with a means of recording cuff pressure as shown by FIG. 4.

Figure 9:
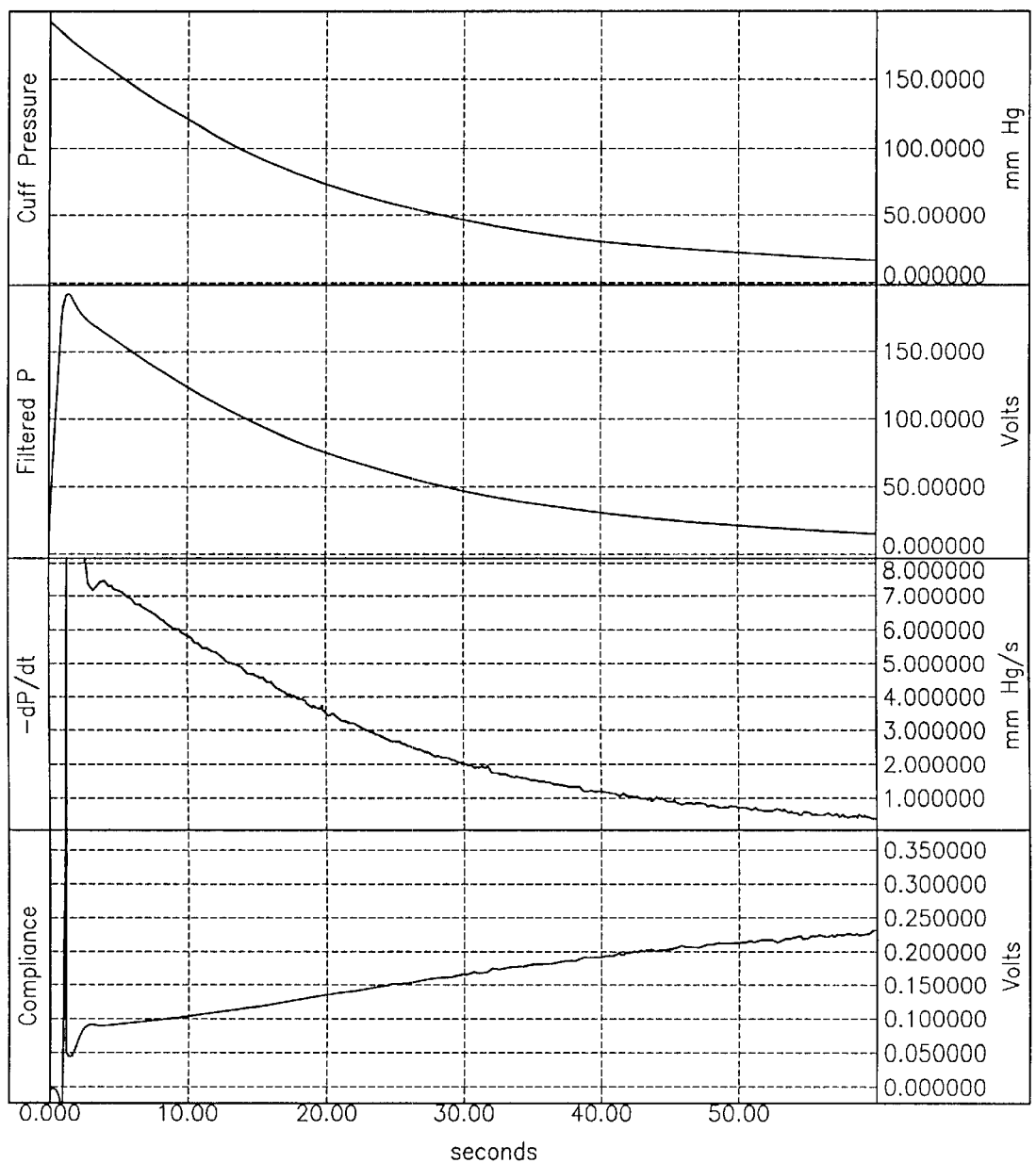
FIG. 9 illustrates a sample recording of cuff pressure and the corresponding calibration of cuff pressure by the system of the present invention.

A sample recording of cuff pressure and the corresponding calibration of cuff pressure is shown by FIG. 9. Four tracings are provided versus time. In this study, the arm cuff 406 was applied around a rigid cylinder, so there is no pulse. The occlusive arm cuff 406 is allowed to deflate through a fixed flow orifice of the flow restrictor 506. This can be seen in the top tracing of raw cuff pressure data. The pressure data was then filtered to remove noise and pulse variations, if present, as shown by the second tracing. The derivative of cuff pressure was then obtained by a numerical algorithm as shown by the third tracing. Then, the cuff compliance was obtained using Equation B. Note that the cuff compliance decreases with cuff pressure as expected. Moreover, note that the compliance changes over a range greater than double the high pressure values. This suggests the importance of determining cuff compliance continuously by the present invention.

It is contemplated to provide a visual indication to inform the user that the data acquisition sequence has started and to also inform the user when to stop inflating the arm cuff 406. When inflation is stopped, the flow restrictor 506 deflates the arm cuff 406 while additional data is recorded in the memory of the microcomputer 510. The data is then transferred or uploaded via the RS-232 cable 402 to the PC 600 for processing. It is contemplated that the data is stored on a PC hard drive and it is post processed using the PC application or analysis software to provide blood pressure compliance and lumen area information.

The output signal provided by the pressure transducer 502 to the A/D converter 508 includes a first component caused by compressed air in the arm cuff 406 by the hand pump 408; and a second component caused by the patient's arterial pulse. The first component is separately analyzed by passing the signal from the pressure transducer 502 through a lowpass filter to produce a first waveform. The second component is separately analyzed by passing the signal from the pressure transducer 502 through a bandpass filter that passes signals having frequencies between 0.5 and 5 Hz. to produce a second waveform.

After data acquisition is completed, the first and second waveforms, along with data regarding the flow restrictor 506, are provided to the at least one processor 204 of the PC 600 to calculate at least the following parameters: systolic and diastolic pressure; arterial compliance; volume of blood flow through the artery per unit time; phase lag between the pressure and blood flow waveforms; arterial lumen area; and cuff compliance. The at least one processor 204 then using the calculated parameters plots arterial pressure versus lumen area curves (P-A curves) and arterial pressure versus compliance curves (P-C curves) and correlates the P-A and P-C curves with the computer models stored in the database 202.

The processor then determines at least one vascular condition of the patient by determining which vascular conditions stored within the database 202 correspond the greatest or are categorized with curves stored within the database 202 closely approximating the P-A and P-C curves produced from the patient arterial data. The results of the analysis are then outputted, e.g., on the display 208, and/or stored. A medical practitioner can also refer to the display 208 for further diagnosing the patient, as well as being able to reasonably determine, based on experience in observing patient arterial data of many patients, where in the vasculature there exists or may exist a particular object, such as a stenotic lesion, or if the patient has a strong potential of developing coronary or cerebral vascular disease.

It is contemplated that the analysis software 206 further includes signal processing instructions in order for the at least one processor 204 to be able to also analyze the first and second waveforms received from the hardware unit 500. The analyzed waveform data can then be correlated with waveform data stored within the database of computer models 202, in a manner similar to correlating the P-A and P-C curves with the P-A and P-C curves stored within the database 202, as discussed above, to diagnose and predict various vascular conditions.

The system of the present invention can further be used to determine endothelial/vascular smooth muscle function. Endothelial function is an important aspect of a blood vessel possessing smooth muscle. In its natural state, the smooth muscle of the blood vessel exerts a constant level of force. This force, in turn, determines the diameter of the vessel and its resistance to blood flow. Current clinical investigations have found that the smooth muscle activity is diminished in the presence of vascular diseases such as hypertension and atherosclerosis. The occlusive arm cuff plethysmograph as provided by the system of the present invention provides a noninvasive means of measuring endothelial or smooth muscle function. Since the method is as simple as a blood pressure determination, it can be used routinely to examine patient populations over several years. It can also be used to measure patient response to drug therapy. Currently, only ultrasound imaging devices are capable of providing this measurement or test which impose considerable cost in performing the test on a routine basis. Furthermore, it requires a skilled operator. Additionally, in some patients with excess adipose tissue, ultrasound cannot obtain a vessel image for analysis. Cuff plethysmography circumvents these problems. A method will now be described in determining a patient's endothelial function using the present invention.

The problem of measuring endothelial function is one of providing an appropriate baseline for which the resting function can be compared. This is accomplished by first using the occlusive arm cuff plethysmograph as implemented by the system of the present invention to find the patient's resting P-A and P-C curves. Next, an additional occlusive arm cuff is applied over the occlusive arm cuff plethysmograph and as far up the arm as possible. This extra cuff is then inflated to approximately 50 mm Hg over the patient's systolic pressure and allowed to remain at this level for a period of approximately five minutes.

Figure 10A:
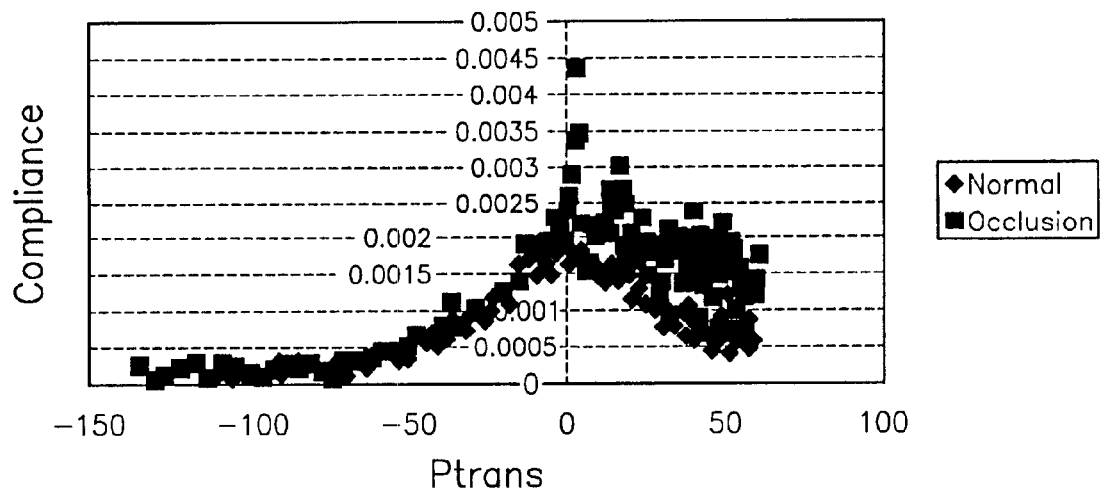
FIG. 10A is a chart plotting the transmural pressure versus compliance, i.e., P-C curve, for a normal and an occluded blood vessel.
Figure 10B:
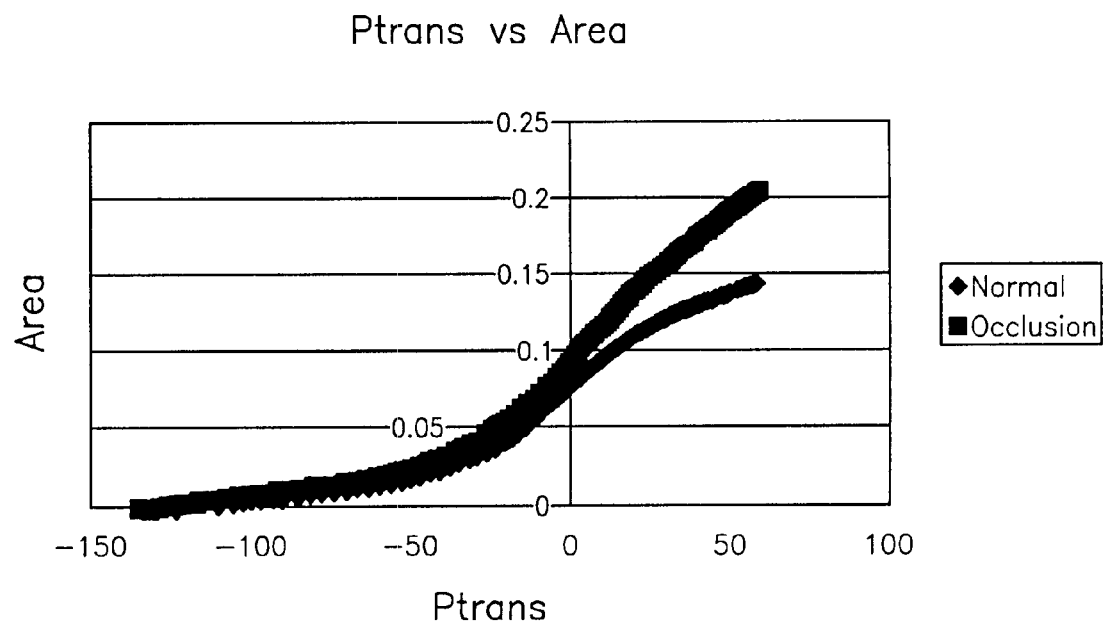
FIG. 10B is a chart plotting the transmural pressure versus lumen area, i.e., P-A curve, for a normal and an occluded blood vessel.

During this time period, the underlying vessels are subjected to a loss of blood supply. This causes a condition referred to as reactive hyperemia, where the arteries vasolidate. The dilation is extensive and forces the smooth muscle to be nearly inactive. Under this condition a maximal P-A curve for the vessel is determined by the embedded software of the hardware unit 500. This maximal vasolidated P-A curve serves as a reference for which the resting P-A curve can be compared. The vasolidated P-A curve is obtained by inflating the plethysmograph cuff 406 as usual and quickly deflating the extra cuff. The embedded software of the hardware unit 500 obtains the measurement. This measurement is the maximal vasolidated P-A or P-C curve. The two recordings, i.e., transmural pressure and lumen area or transmural pressure and compliance, are then plotted on the same graph for comparison as shown by FIGS. 10A and 10B. From FIGS. 10A and 10B, it can be seen that occlusion generally causes the arterial lumen and compliance to both increase at all pressures relative to the normal or resting curves. The effect is more pronounced at high positive pressures. This is expected for vasolidation.

In one method of comparison, the two P-A curves can be subtracted. That is, the pressure of each curve is subtracted at their corresponding area. The result of this subtraction is physiologically related to the endothelial function or smooth muscle force in the wall of the vessel.

The vasolidated P-A and P-C curves can be stored in an individual patient database within the database 202 and provide a baseline measurement of vascular endothelial function for the specific patient. The vasolidated P-A and P-C curves can also be compared with established functional response for the general subject population.

It is contemplated that the patient's vascular endothelial function can be determined after having used the system of the present invention to the determine the patient's resting P-A and P-C curves. That is, the additional occlusive arm cuff is placed over the patient's brachial artery after the occlusive arm cuff 406 has been inflated to determine patient vascular data and subsequently deflated.

It will be understood that various modifications can be made to the various embodiments of the present invention herein disclosed without departing from its spirit and scope. Therefore, the above description should not be construed as limiting the invention but merely as presenting preferred embodiments of the invention. Those skilled in the art will envision other modifications within the scope and spirit of the present invention as defined by the claims presented below.

What is claimed is:

1. A system for determining one of at least one vascular condition and endothelial function, comprising:

an occlusive arm cuff plethysmograph having at least one occlusive arm cuff for placement over a patient's brachial artery, means for obtaining patient vascular data and means for outputting said patient vascular data;

at least one database storing predetermined vascular data and a plurality of corresponding vascular conditions;

a plurality of programmable instructions, for (1) correlating said patient vascular data with said predetermined vascular data stored within said at least one database and determining at least a portion of said predetermined vascular data which exhibits the maximum correlation with said patient vascular data, wherein said at least one vascular condition is determined to be at least one of said plurality of corresponding vascular conditions which corresponds to a portion of said predetermined vascular data, and (2) determining endothelial function using said patient vascular data; and at least one processor for executing at least one of said correlating or said determining endothelial function.

2. The system according to claim 1, wherein said means for obtaining patient vascular data comprises:

a flow restrictor for receiving a pressure input from said occlusive arm cuff and outputting a pressure output according to a flow resistance parameter, R, characteristic of said flow restrictor;

a pressure transducer for receiving said pressure output and transmitting at least one pressure reading output; and a processor for receiving said at least one pressure reading output from said pressure transducer and determining vascular measurements based on said at least one pressure reading output.

3. The system according to claim 1, further comprising:

a hand pump connected to said occlusive arm cuff; and a pressure gage connected to said occlusive arm cuff via a T-connector.

4. The system according to claim 3, wherein said occlusive arm cuff, said hand pump and said pressure gage comprise a blood pressure monitor.

5. The system according to claim 1, wherein said predetermined vascular data includes a plurality of computer models.

6. The system according to claim 1, wherein said means for outputting said vascular data outputs said patient vascular data as at least one waveform.

7. The system according to claim 1, further comprising at least one display for displaying data.

8. The system according to claim 1, wherein said at least one database is located at a remote location and said at least one processor accesses said at least one database via a network data connection.

9. The system according to claim 1, wherein said at least one processor is connected to said occlusive arm cuff plethysmograph via an analog-to-digital converter.

10. The system according to claim 1, wherein said plurality of programmable instructions are stored within a memory of said at least one processor.

11. The system according to claim 1, wherein said at least one processor and said at least one database are remotely located from said occlusive arm cuff plethysmograph.

12. The system according to claim 1, wherein said predetermined vascular data includes arterial pressure versus lumen area curves (P-A curves).

13. The system according to claim 1, wherein said predetermined vascular data includes arterial pressure versus compliance curves (P-C curves).

14. A method for determining one of at least one vascular condition and endothelial function, comprising the steps of:

providing an occlusive arm cuff plethysmograph having at least one occlusive arm cuff for placement over a patient's brachial artery, means for obtaining patient vascular data and means for outputting said patient vascular data;

placing said occlusive arm cuff plethysmograph over said patient's brachial artery;

inflating said at least one occlusive arm cuff, obtaining said patient vascular data by said means for obtaining patient vascular data, and outputting said patient vascular data by said means for outputting;

providing at least one database storing predetermined vascular data and a plurality of corresponding vascular conditions; and providing a plurality of programmable instructions for (1) correlating said patient vascular data with said predetermined vascular data stored within said at least one database and determining at least a portion of said predetermined vascular data which exhibits the maximum correlation with said patient vascular data, wherein said at least one vascular condition is determined to be at least one of said plurality of corresponding vascular conditions which corresponds to a portion of said predetermined vascular data, and (2) determining endothelial function using said patient vascular data; and executing by at least one processor at least one of said correlating or said determining endothelial function.

15. The method according to claim 14, wherein said predetermined vascular data includes a plurality of computer models.

16. The method according to claim 14, further comprising the step of displaying said at least one determined vascular condition.

17. The method according to claim 14, further comprising the step of accessing said at least one database via a network connection.

18. The method according to claim 14, further comprising the step of predicting at least one vascular condition by correlating said patient vascular data with said predetermined vascular data.

19. The method according to claim 14, further comprising the step of storing said patient vascular data within said at least one database.

20. The method according to claim 14, wherein the step of determining endothelial function using said patient vascular data further comprises the steps of:

deflating said at least one occlusive arm cuff, placing an additional occlusive arm cuff over the patient's brachial artery;

inflating said additional occlusive arm cuff over the patient's systolic pressure and maintaining said additional occlusive arm cuff over the patient's systolic pressure for a predetermined time period;

inflating said at least one occlusive arm cuff and deflating said additional occlusive arm cuff to obtain vasodilated vascular patient data; and determining endothelial function of the smooth muscle wall of the patient's brachial artery using said vasodilated vascular patient data.

21. The method according to claim 20, wherein said step of inflating said additional occlusive arm cuff entails inflating said occlusive arm cuff to 50 mm Hg over the patient's systolic pressure.

22. The method according to claim 20, wherein said predetermined time period is approximately five minutes.

23. The method according to claim 20, further comprising the step of storing said vasodilated vascular patient data within said at least one database.

24. A system for determining at least one vascular condition, comprising:

an occlusive arm cuff plethysmograph having a first occlusive arm cuff for placement over a patient's brachial artery, means for obtaining patient vascular data and means for outputting said patient vascular data;

at least one database storing predetermined vascular data and a plurality of corresponding vascular conditions;

a second occlusive arm cuff for placement over the patient's brachial artery;

means for obtaining vasodilated patient vascular data using the first and second occlusive arm cuffs, a plurality of programmable instructions, executed for correlating said patient vascular data with said predetermined vascular data stored within said at least one database for determining at least a portion of said predetermined vascular data which exhibits the maximum correlation with said patient vascular data, wherein said at least one vascular condition is determined to be at least one of said plurality of corresponding vascular conditions which corresponds to a portion of said predetermined vascular data, and determining endothelial function of the smooth muscle wall of the patient's brachial artery using said vasodilated patient vascular data; and at least one processor for executing at least one of said correlating or said determining endothelial function.

25. A method for determining at least one vascular condition, comprising the steps of providing an occlusive arm cuff plethysmograph having an occlusive arm cuff for placement over a patient's brachial artery, means for obtaining patient vascular data and means for outputting said patient vascular data;

placing said occlusive arm cuff plethysmograph over said patient's brachial artery;

inflating said occlusive arm cuff, obtaining said patient vascular data by said means for obtaining patient vascular data, and outputting said patient vascular data by said means for outputting;

providing at least one database storing predetermined vascular data and a plurality of corresponding vascular conditions;

executing by at least one processor a plurality of programmable instructions for correlating said patient vascular data with said predetermined vascular data stored within said at least one database and determining at least a portion of said predetermined vascular data which exhibits the maximum correlation with said patient vascular data, wherein said at least one vascular condition is determined to be at least one of said plurality of corresponding vascular conditions which corresponds to a portion of said predetermined vascular data;

deflating said occlusive arm cuff, placing an additional occlusive arm cuff over the patient's brachial artery;

inflating said additional occlusive arm cuffover the patient's systolic pressure and maintaining said additional occlusive arm cuff over the patient's systolic pressure for a predetermined time period;

inflating said occlusive arm cuff and deflating said additional occlusive arm cuff to obtain vasodilated vascular patient data; and determining endothelial function of the smooth muscle wall of the patient's brachial artery using said vasodilated vascular patient data.

* * * * *